United States Patent [19]

Ishikawa et al.

[11] Patent Number: 4,652,735
[45] Date of Patent: Mar. 24, 1987

[54] IMAGE READER FOR X-RAY FILM OR THE LIKE HAVING A DETECTION SYSTEM WITH AN EXPANDED DYNAMIC RANGE

[75] Inventors: Ken Ishikawa; Mitsuru Ikeda; Shigeru Watanabe, all of Chiba, Japan

[73] Assignee: Hitachi Medical Corporation, Japan

[21] Appl. No.: 605,408

[22] Filed: Apr. 30, 1984

[51] Int. Cl.$^4$ .......................... H01J 40/14; G01J 1/42
[52] U.S. Cl. ...................................... 250/578; 356/224
[58] Field of Search ............... 250/562, 563, 559, 578, 250/566, 572, 330; 356/222, 224

[56] References Cited

U.S. PATENT DOCUMENTS 3,781,558 12/1973 Anderson ............................ 250/330

*Primary Examiner*—Gene Wan
*Attorney, Agent, or Firm*—Gerald J. Ferguson, Jr.; Michael P. Hoffman; Ronni S. Malamud

[57] ABSTRACT

An image reader having a high sensitive detection system for detecting a variation in a first light quantity to generate a first output, a low sensitive detection system for detecting a variation in a second light quantity to generate a second output where the second light quantity is greater than the said first light quantity, and a signal composing circuit for receiving the outputs of the high and low sensitive detection systems, each of the detection systems being so disposed as to detect simultaneously or substantially simultaneously a ray bundle from a picture element of a picture, and the output of the signal composing circuit being (a) the output of the high sensitive detection system when the received light quantity is smaller than a threshold light quantity which can be detected with substantially the same degree of accuracy by both the detection systems or (b) the sum of (i) the output of the low sensitive detection system and (ii) the difference between the outputs of the detection systems at the threshold light quantity whereby a time-serial output of wide dynamic range is obtained.

2 Claims, 13 Drawing Figures

IMAGE READER FOR X-RAY FILM OR THE LIKE HAVING A DETECTION SYSTEM WITH AN EXPANDED DYNAMIC RANGE

BACKGROUND OF THE INVENTION

This invention relates to an image or picture reader and, particularly, to an image reader which measures or photometers, on scanning the whole image or picture area, the quantity of transmitted light, reflected light or luminescence light given from individual picture elements comprising the picture and outputs a time-serial electric signal reflecting the measured results, for the purpose of preserving, processing or forwarding the image information.

An image reader reads the image information of an object picture by detecting the variation in quantity of transmitted, reflected or luminescene light given from individual picture elements. However, this light quantity varies over a wide dynamic range in general. For example, the dynamic range of transmitted light from an X-ray film extends over a fixed quantity of incident light, four digits of magnitude in the case of diffuse density photometry, or six to eight digits of magnitude in the case of specular density photometry. Also, the quantity of light emitted by a fluorescent screen used in X-ray fluoroscopy gives a dynamic range of six or more digits.

Contrary to the above, the dynamic range of detection systems employed in conventional image readers is restricted by the dynamic range of detectors and amplifiers making up the detection system and gives four digits of magnitude at the most. For example, a CCD (charge coupled device) has a two-digit dynamic range, a camera tube gives three digits or so, and an amplifier has a dynamic range only in the order of three to four digits where all of these components serve as the detector.

Therefore, since a conventional image reader has a detection system whose dynamic range is less than that of the light quantity from the object picture, it cannot fully read the image information of this picture.

SUMMARY OF THE INVENTION

It is an object of this invention to overcome the drawbacks of the prior art devices and to provide an improved image reader which can fully read the image information of an object picture over a wide dynamic range.

The novel feature of the image reader according to this invention is that its photometry section simultaneously or substantially simultaneously photometers the transmitted, reflected or luminescence light given from individual picture elements by means of plural detection systems which differ from one another in overall sensitivity inclusive of converging efficiency. The output section of the image reader selects from the plural output signals of the foregoing detection systems and composes therefrom a time-serial electric signal reflecting the light quantity from the picture elements, whereby the dynamic range of the reader is expanded as a whole.

DESCRIPTION OF THE PREFERRED EMBODIMENTS

Figure 1:
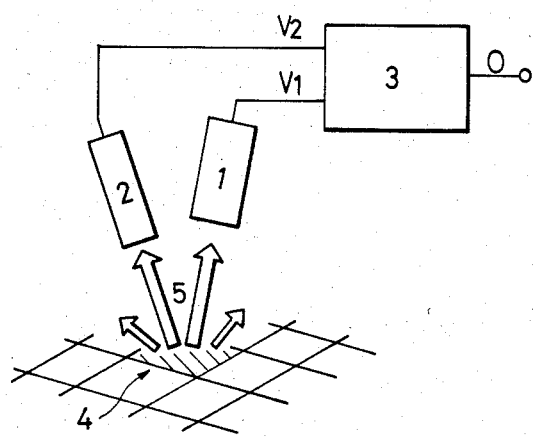
FIG. 1 is a basic schematic diagram showing the functional principle of this invention.

FIG. 1 is a schematic diagram showing the functional principle of this invention, including two detection systems as an example. 1 is a high sensitive detection system, 2 is a low sensitive detection system, 3 is a signal composing circuit, 4 is a picture element of a picture, and 5 is transmitted light, reflected light or luminescense light from the picture element. Further, $V_1$ is an output signal of the high sensitive detection system, $V_2$ is an output signal of the low sensitive detection system, and O is an output signal of the signal composing circuit.

The high sensitive detection system 1 is a detection system which can measure at a high degree of accuracy the variation in light quantity in case the quantity of light of a bundle of rays from picture element 4 is small and low sensitive detection system 2 is a detection system which can measure at a high degree of accuracy the variation in light quantity in case the light quantity is large.

The bundle of rays given by transmission, reflection or emission at picture element 4 is photometered simultaneously or substantially simultaneously by high sensitive detection system 1 and low sensitive detection system 2, these systems differ from each other in overall sensitivity inclusive of converging efficiency. The resultant signals are converted respectively into high sensitive detection system output signal $V_1$ and low sensitive detection system output signal $V_2$ and then applied to signal composing circuit 3.

In general, the high sensitive detection system output signal $V_1$ and/or the low sensitive detection system output signal $V_2$ applied to the signal composing circuit 3 are compared with a threshold, and either output signal $V_1$ or $V_2$ is selected depending upon the compared results being large or small. These output signals are subjected to a connection process in accordance with the overall gain ratio of the detection systems 1 and 2 whereby the output signal O in the form of a time-serial electric signal is produced.

The foregoing selection process and connection process in signal composing circuit 3 will be described with reference to FIGS. 2 and 3.

Figure 2:
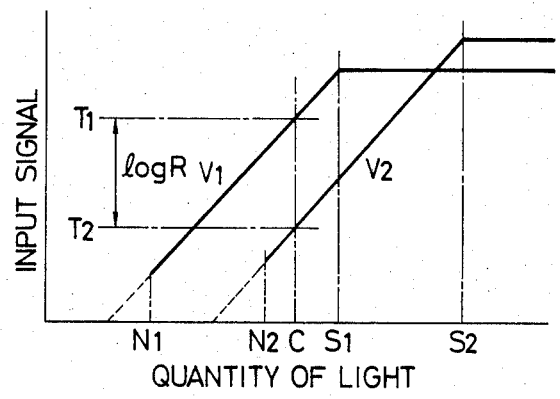
FIG. 2 is a graph showing the dynamic ranges of input signals for a signal composing circuit.

FIG. 2 shows the dynamic ranges of the input signals $V_1$ and $V_2$. The horizontal axis represents the quantity of transmitted, reflected or luminescence light 5 given from picture element 4 in a logarithmic scale and the vertical axis represents the input signal for signal composing circuit 3 in a logarithmic scale. In this drawing, $N_1$ and $N_2$ are minimum detectable light quantities of high sensitive detection system 1 and low sensitive system 2, respectively, while $S_1$ and $S_2$ are maximum detectable light quantities of high sensitve detection system 1 and low sensitive detection system 2, respectively.

The interval between $N_1$ and $S_1$ is the dynamic range of high sensitive detection system 1 while the interval between $N_2$ and $S_2$ is the dynamic range of low sensitive detection system 2. By appropriately selecting a converging efficiency ratio, a detector sensitivity ratio and an amplifier gain ratio between high sensitive detection system 1 and low sensitive detection system 2, the dynamic ranges of both detection systems can be made to overlap each other. That is, the relation $N_2 < S_1$ can be obtained. A light quantity threshold indicated by "C" in FIG. 2 and intermediate $N_2$ and $S_1$ may then be set where $T_1$ and $T_2$ represent the output signals of the high sensitive detection system 1 and low sensitive detection system 2, respectively, corresponding to light quantity threshold C.

As shown by the bold lines in FIG. 2, in case $V_1$ is to be compared with the threshold, the signal composing circuit 3 selects $V_1$ if $V_1 < T_1$ or $V_2$ if not $V_1 < T_1$. If $V_2$ is to be compared with the threshold, $V_1$ is selected if $V_2 < T_2$ or $V_2$ is selected if not $V_2 < T_2$. In addition, in order to connect the bold lines shown in FIG. 2 at connection point C and change them into one straight output (characteristic curve), these outputs are processed using the overall gain ratio R of both detection systems indicated in FIG. 2, as will be further discussed below with respect to FIG. 5.

Figure 3:
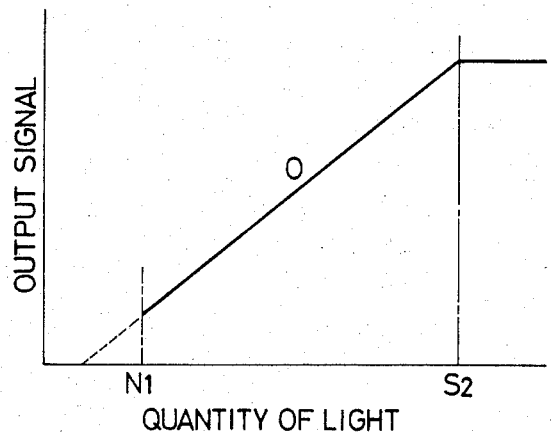
FIG. 3 is a graph showing a dynamic range of an output signal from the signal composing circuit according to this invention.

FIG. 3 shows the dynamic range of the output signal of signal composing circuit 3 after the foregoing process has been effected. In this figure, the horizontal axis also represents the quantity of transmitted, reflected or luminescence light from picture element 4 in a logarithmic scale and the vertical axis represents the output signal of signal composing circuit 3 in a logarithmic scale. Accordingly, it will be understood that the dynamic range of the output signal O of signal composing circuit 3 is expanded and extended from $N_1$ to $S_1$ as the result of the foregoing processes.

Though the basic arrangement shown in FIG. 1 includes the two routes of detection systems, it is also possible to employ three or more detection systems differing one another in sensitivity, to set plural light quantity thresholds in the signal composing circuit for achieving the selection and connection processes and, thereby to effect a composite detection system with a further expanded dynamic range.

Several embodiments of the image reader according to this invention will be described below.

Figure 4:
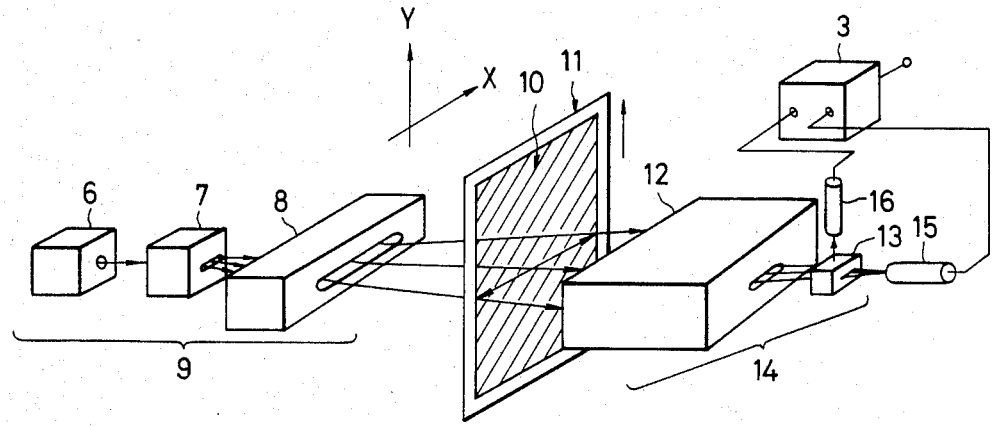
FIG. 4 is a schematic diagram showing an embodiment of a transmitted light type image reader according to this invention.

FIG. 4 shows an embodiment of an image reader of the transmitted light type according to this invention. In this drawing, 6 is a light source, 7 is a one-dimensional optical deflector, 8 is an incidence-side converging optical system, 10 is a picture medium such as an X-ray film, 11 is a sample holder movable in the direction of the arrow (the Y-direction) member, 12 is a converging member, 13 is an optical distributor, 15 is a first light detection system, 16 is a second light detection system, and 3 is the signal composing circuit. It does not matter whether first detection system 15 and second detection system 16 are correspondingly the high sensitive detection system and the low sensitive detection system or vice versa, as will be described hereinafter. The light source 6, one-dimensional optical deflector 7 and incidence-side converging optical system 8 make up a minute ray bundle one-dimensional optical scanner 9. The converging member 12 and optical distributor 13 make up a converging dispatching system 14.

The direction of the bundle of rays emitted from light source 6 is changed within one plane by one-dimensional deflector 7. The bundle of rays passed through the one-dimensional deflector 7 is converged onto a minute area corresponding to a picture element on picture medium 10 by means of incidence-side converging optical system 8 comprising a condenser lens, condenser mirror or the like. In this manner, scanner 9 causes the bundle of rays, whose minute sectional area corresponds to the size of the picture element, to scan the picture medium along one straight line (the X-direction in the drawing). Since picture medium 10 is also conveyed in the Y-direction, which is orthogonal to the scanning direction of the minute bundle of rays, the ray bundle of minute sectional area two-dimensionally scans the picture medium.

The bundle of rays applied to the minute area corresponding to a picture element of picture medium 10 is transformed into transmitted light bearing a transmission density information and enters converging member 12. This member 12 converges the transmitted light from each picture element onto a light detection system comprising a condenser lens, condenser mirror, optical fiber bundle or the like. Through the optical distributor 13 disposed behind converging member 12 the transmitted light is directed onto first and second light detection systems 15 and 16 where the outputs of both detection systems are applied to singal composing circuit.

In the foregoing arrangement, the minute ray bundle one-dimensional scanner 9 can be modified so that the one-dimensional deflector 7 be disposed behind the incidence-side converging optical system 8. In place of the light source 6 and the incidence-side converging optical system 8, a minute parallel ray pencil generator can be employed. In place of the one-dimensional deflector 7, the light source 6 and the incidence-side converging optical system 8, or the minute parallel ray pencil generator, can be rotated about one axis to produce same result. As the one-dimensional deflector 7, other members such as rotary mirror, rotary polygonal mirror, vibratory mirror such as galvanometer, electro-optic deflector, or acousto-optic deflector, can also be employed.

The optical distributor 13 can comprise a beam splitter, a combination of a beam splitter and relay lens, or an optical fiber bundle which can distribute a bundle of rays which enters through a single incident port into plural outgoing ports. And the same result can be obtained without the optical distributor 13, arranging the light-receiving sections of the first light detection system 15 and the second 16, so that these sections may be irradiated simultaneously by the ray bundle converged by the converging member 12. The converging distributing system 14 comprising the converging member 12 and the optical distributor 13 can be modified so that two routes of converging members 12 be disposed behind optical distributor 13, or the same be composed only of two routes of converging members 12 differing from each other in the direction of observing each picture element. The light detection systems 15 and 16 each generally comprise a light detector and amplifier circuitry but may further include an optical filter for adjustment of sensitivity.

As other methods for causing the ray bundle of minute sectional area to two-dimensionally scan the picture medium 10, there is the method of two-dimensionally conveying the picture medium while the minute bundle of rays is kept stationary and the method of causing a two-dimensional scanning movement of the minute bundle of rays as the picture medium is kept stationary. In either method, similarly to the foregoing embodiment, the basic arrangement shown in FIG. 1 can be realized by inclusion of the converging distributing system 14, the two routes of light detection systems 15 and 16, and signal composing circuit 3.

Figure 5:
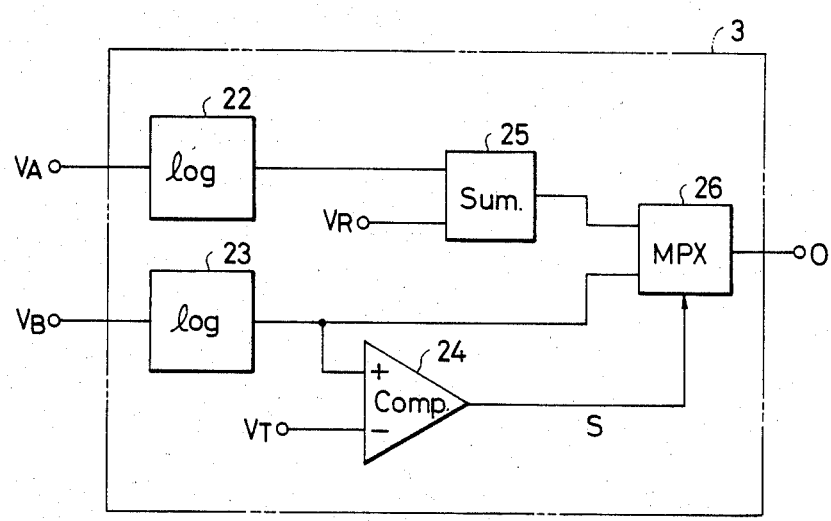
FIG. 5 is a block circuit diagram showing an embodiment of the signal composing circuit according to this invention.

Signal composing circuit 3 will not be described. It is this circuit which effects the selection and connection processes with respect to the output signals from detection systems 15 and 16 where detectors 15 and 16 detect the quantity of light from the picture element. FIG. 5 shows one embodiment of signal composing circuit 3, it being an analogue circuit comprising first and second logarithmic converters 22 and 23, a comparator 24, an adder 25, and a multiplexer 26. Denoting the input signals given from the two routes of the detection system by $V_A$ and $V_B$, these signals are first logarithmically converted into signals proportional to $\log V_A$ and $\log V_B$, respectively. The output, $\log V_B$, of second logarithmic converter 23 is applied to comparator 24 where it is compared with a threshold signal $V_T$. Here, the threshold signal $V_T$ is set to a value corresponding to $\log T_1$ which is the logarithm of $T_1$ shown in FIG. 2 in the case where input signal $V_B$ is the output signal of the high sensitive detection system which may either be detection system 15 or 16, or, in the case where input signal $V_B$ is the output signal of the low sensitive detection system, the threshold signal $V_T$ is set to a value corresponding to $\log T_2$ which is the logarithm of $T_2$. The output, $\log V_A$, of first logarithmic converter 22 is applied to adder 25 where a detection system gain ratio signal $V_R$ is added thereto. The detection system gain ratio signal $V_R$ is set on the basis of the ratio of $V_A$ and $V_B$ lying in an interval where the dynamic ranges of the two routes of the detection system overlap each other in accordance with the following equation:

$$V_R = -\log(V_A/V_B) \quad (1)$$

The output, $\log V_A + V_R$, of adder 25 and the output, $\log V_B$, of second logarithmic converter 23 are applied to multiplexer 26 where either output is selected in accordance with the output S of comparator 24. That is, in the case where $V_A$ is the output signal of the high sensitive detection system and the $V_B$ is the output of the low sensitive detection system, the $\log V_B$ is selected and outputted if $\log V_B > V_T$ where $V_T \propto \log T_2$, or the $\log V_A + V_R$ is selected and outputted if $\log V_B \leq V_T$. Contrarily, in case the $V_A$ is the output signal of the low sensitive detection system and the $V_B$ is the output signal of the high sensitive detection system, the reverse selection of outputs is effected where $V_T \propto \log T_1$, as discussed above. In this way, by selecting the plural output signals from the detection systems and composing therefrom a time-serial electric signal reflecting the light quantity from the picture elements, an output signal O of wide dynamic range is obtained as shown in FIG. 3.

Though the foregoing description is related to the embodiment of an image reader of the transmitted light type, this invention can be modified into different types, such as a reflected light type or a luminescense light type. Other principle embodiments of this invention will now be described.

Figure 6:
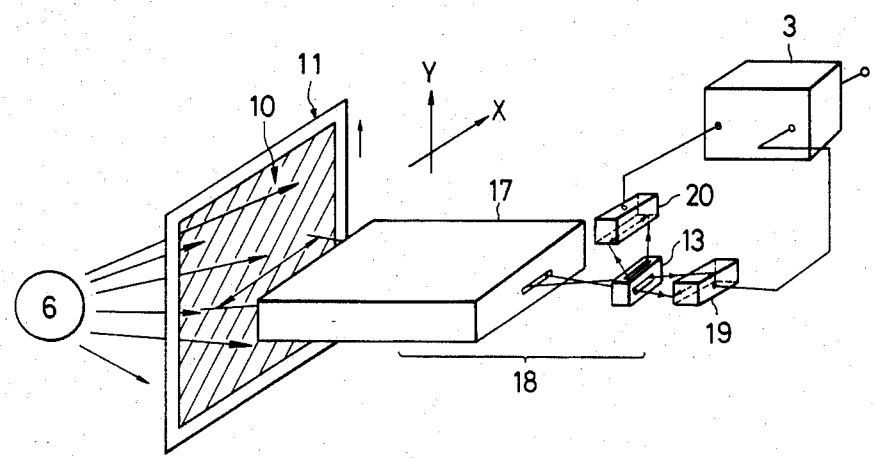
FIG. 6 is a schematic diagram showing another embodiment of the transmitted light type image reader according to this invention.

FIG. 6 shows another embodiment of the image reader of the transmitted light type according to this invention. In this drawing, 6 is the light source, 10 is the picture medium, 11 is the movable sample holder, 17 is an imaging optical system, 13 is the optical distributor, 19 is a first line detection system, 20 is a second line detection system, and 3 is the signal composing circuit, the imaging optical system 17 and the optical distributor 13 making up an imaging distributing system 18. The line detection systems are devices which can read or detect on a time-serial basis the light quantity received at successive points forming a linear light-receiving section. Similarly to the foregoing embodiment, it does no matter whether the first and second detection systems are correspondingly to be the high and low sensitive detection systems or vice versa, since this can be adjusted in signal composing circuit 3.

The light emitted by source 6 is transmitted through picture medium 10 and forms a transmission image on the side of the imaging optical system 17. Optical system 17 forms the real image of the transmission image on the light-receiving section of the line detection system and may comprise an imaging lens, imaging mirror or the like. Behind imaging optical system 17 optical distributor 13 is disposed which forms the real image of the transmission image on the light-receiving sections of first and second line detection systems 19 and 20, whereby the density information at portions along one straight line (the X-direction in the drawing) on the transmission image is read out. By conveying the picture medium 10 in the Y-direction, a two-dimensional read-out of the image is achieved.

By applying the outputs of both line detection systems to signal comprising circuit 3, the basic arrangement of FIG. 1 is effected. That is, the output signals of line detection systems 19 and 20 are composed by signal composing circuit 3 as described in connection with the foregoing embodiment of FIG. 5 and converted into the output signal O of wide dynamic range.

The imaging distributing system 18 comprising imaging optical system 17 and optical distributor 13 can be modified so that two routes of imaging optical systems 17 are disposed behind optical distributor 13, or, only two routes of imaging optical systems differing from each other in the direction of observing the transmission image are sufficient. Also, by moving the whole photometering system including the imaging optical system 17 and the like in the Y-direction or by rotating the same about an axis extending in the X-direction, with picture medium 10 being kept stationary, two-dimensional read-out is possible.

Though a line detection system generally comprises a line detection section including a line sensor and a line sensor driving circuit and an amplifier, its line detection section can also be realized by moving such a point detection section along a straight line, that is made up of a point sensor or a combination of a pin hole and a photo detector. Also, by inclusion of an optical filter within the line detection system, adjustment of sensitivity is possible.

As the method of forming the real image of the transmission image on the light-receiving section of the detection system and reading the same, it is also possible to employ a method of utilizing a point detection system comprising a point detection section and an amplifier, or a plane detection system. In the method of utilizing the point detection system, there are different kinds; a first where the picture medium is conveyed two-dimensionally, a second where the picture medium is conveyed one-dimensionally with the point detection system being moved or rotated, and a third where the point detection system is moved or rotated to subjected to both.

Another type of image reader is the reflected light type. In a reflected light type of image reader, the light source or the minute ray bundle generating/scanning section is positioned on the same side of the sample picture as that of the converging member or the imaging optical system. This arrangement of a reflected light type can also effect the basic arrangement shown in FIG. 1 as the image reader of the transmitted light type does.

Figure 7:
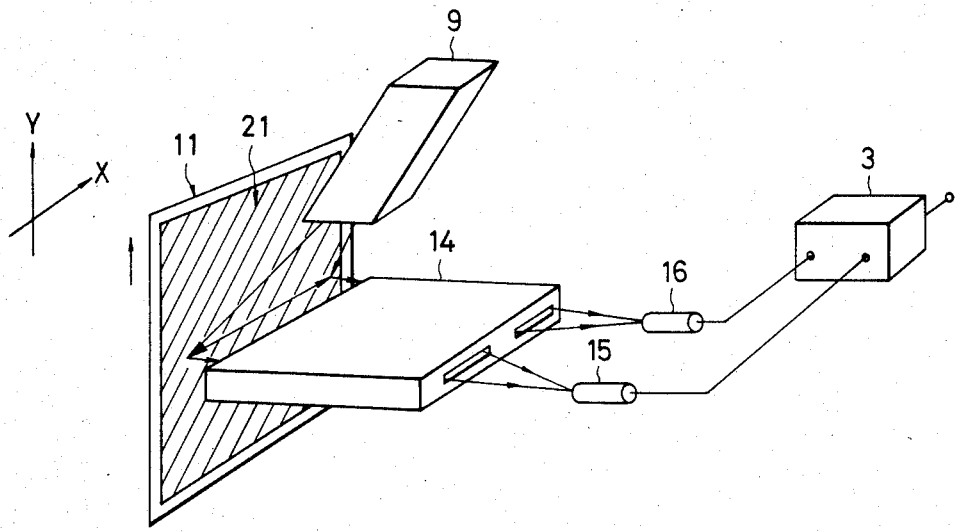
FIG. 7 is a schematic diagram showing an embodiment of a reflected light type image reader according to this invention.

FIG. 7 is the overall schematic diagram showing an embodiment of a reflected light type image reader where 9 is a minute ray bundle one-dimensional scanner, 21 is a picture medium giving a reflected light, 11 is the movable sample holder, 14 is the converging distributor, 15 is a first light detection system, 16 is a second light detection system, and 3 is the signal composing circuit.

The ray bundle having scanned the picture medium 21 is transformed into a reflected light bearing reflection density information and received and distributed by converging distributor 14, and converged onto first light detection system 15 and second light detection system 16. The outputs of both detection systems are subjected to selection and connection processes, in signal composing circuit 3 as described for example, in connection with the embodiment of FIG. 5 and converted into the output signal O of wide dynamic range. Similarly to the transmitted light type image reader of FIG. 4, this embodiment also effects the basic arrangement of FIG. 1 by inclusion of the converging distributor, the two routes of light detection systems, and the signal composing circuit.

In this reflected light type image reader, the real image of the reflected image can also be read out by forming the image on the light-receiving section of the detection system, similarly to the transmitted light type image reader of FIG. 6, which can be comprised of the image distributor, the two routes of point, line or plane detection systems, and the signal composing circuit.

Other than the foregoing types, there is the luminescence light type image reader. This type can be realized by substituting an excitation beam source or an excitation beam bundle one-dimensional scanner for light source 8 or minute ray bundle one-dimensional scanner 9 employed in the image readers of the transmitted light type or reflected light type, and by a picture medium capable of luminescence. That is, a photoluminescence image reader can be realized by using light as the excitation beam, an X-ray luminescence image reader can be realized by using X-ray, a cathode-ray luminescence image reader can be realized by using cathode-ray. Further, in an image reader for a picture medium capable of other types of luminescence, such as electroluminescence, thermoluminescence, chemiluminescence, triboluminescence, sololuminescence, can be realized with the inclusion of the basic arrangement shown in FIG. 1.

The foregoing description relates to several embodiments of this invention, particularly, to the photometering systems. Other principle embodiments of the photometering systems and performing the selection and connection processes thereupon will be described hereinafter.

Figure 8:
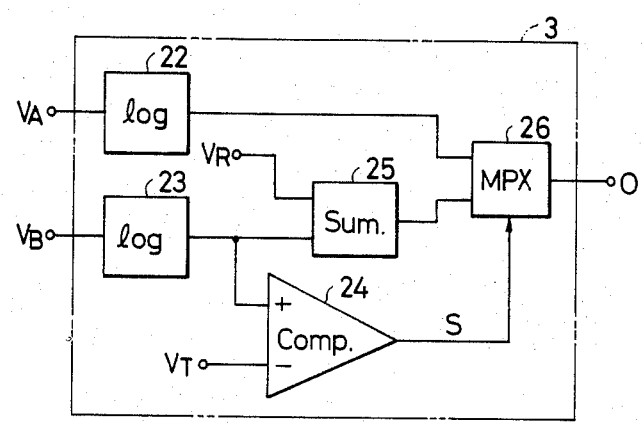
FIG. 8 is a block circuit diagram showing another embodiment of the signal composing circuit according to this invention.

FIG. 8 shows another embodiment of signal composing circuit 3. In this embodiment, adder 25 is disposed on the $V_B$ side in contrast to FIG. 5. Thus, the same function as that of the circuit shown in FIG. 5 can also be obtained in this embodiment if the value of the detection system gain ratio signal $V_R$ is set in accordance with the following equation in place of equation (1):

$$V_R = \log (V_A/V_B) \qquad (2)$$

Figure 9:
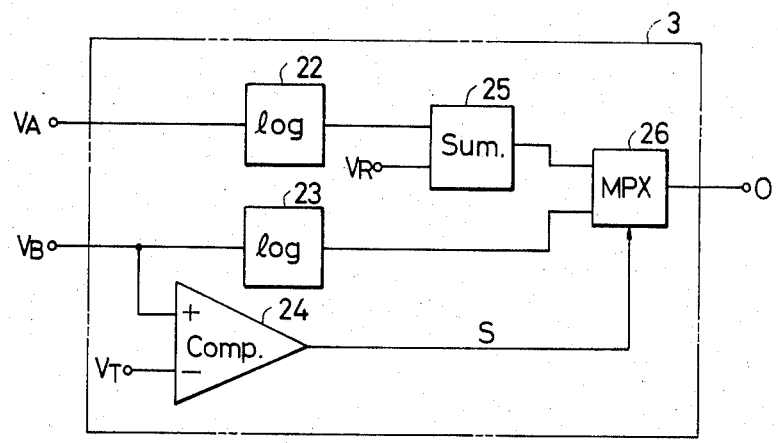
FIG. 9 is a block circuit diagram showing still another embodiment of the signal composing circuit.

FIG. 9 shows still another embodiment of circuit 3 which differs from the embodiment shown in FIG. 5 in that comparator 24 is disposed before second logarithmic converter 23. In this embodiment, the same function as that of the circuit shown in FIG. 5 can be obtained if the value of the threshold signal $V_T$ is set to $T_1$ or $T_2$ as described before with respect to FIG. 5.

Though the foregoing embodiments of signal composing circuit 3 comprise an analogue circuitry, the whole or a portion of circuit 3 can be realized by digital circuitry.

Figure 10:
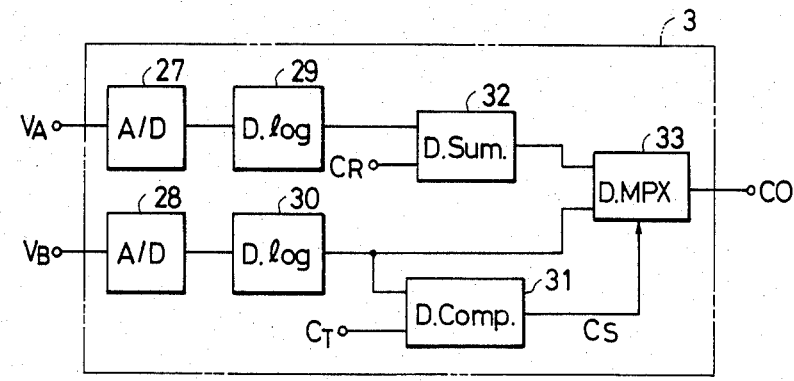
FIG. 10 is a block circuit diagram showing an embodiment of a signal composing circuit including digital components.

FIG. 10 shows an embodiment whose structural elements relating to the elements of the circuit shown in FIG. 5 are replaced by digital elements with first and second analogue/digital (hereinafter abbreviated to A/D) converters 27 and 28 being added in the signal input section. The input signals $V_A$, $V_B$ from the photometering system are digitized by A/D converters 27 and 29, and further converted by first and second digital logarithmic converters 29 and 30. And in place of the threshold signal $V_T$ and the detection system gain ratio signal $V_R$, digital signals representing the threshold $C_T$ and the detection system gain ratio $C_R$ are applied to a digital comparator 31 and a digital adder 32. The selection process is performed in a digital multiplexer 33, and its output becomes a digital signal representing an output value CO corresponding to the value of the output signal O shown in FIG. 5.

Figure 11:
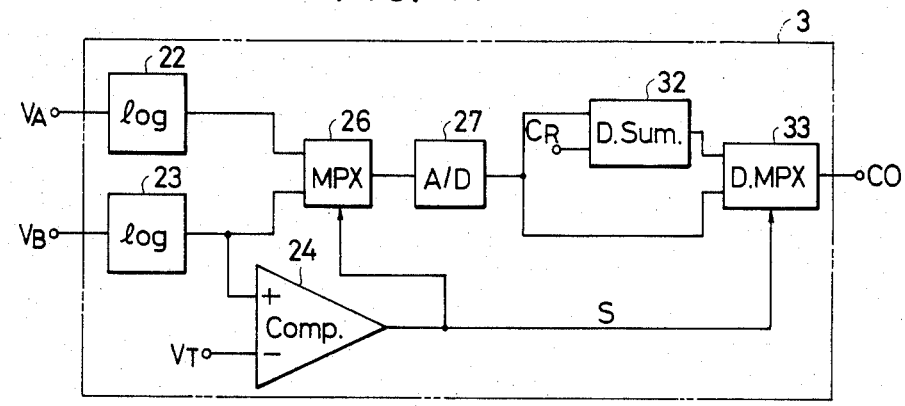
FIG. 11 is a block circuit diagram showing another embodiment of a signal composing circuit including digital components.

FIG. 11 shows a still further embodiment where a portion of the circuit shown in FIG. 5 is transformed into a digital circuit version. In this circuit, multiplexer 26 is disposed before the A/D converter 27, so that the digital circuit version is realized by only one A/D converter.

Figure 12:
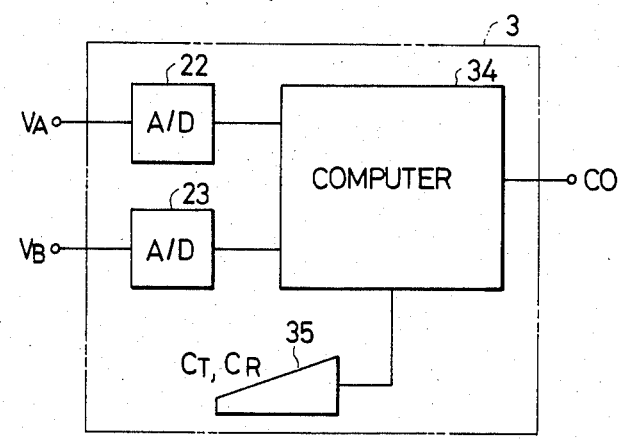
FIG. 12 is a block circuit diagram showing still another embodiment of a signal composing circuit utilizing a digital computer.

In addition, in the signal composing circuits including digital circuit elements, these digital circuit portions can be replaced by a digital computer. FIG. 12 shows a block diagram to realize the function of signal composing circuit 3, which includes a digital computer 34 and an input device 35. This embodiment achieves the same function as that of the signal composing circuit of FIG.

Figure 13:
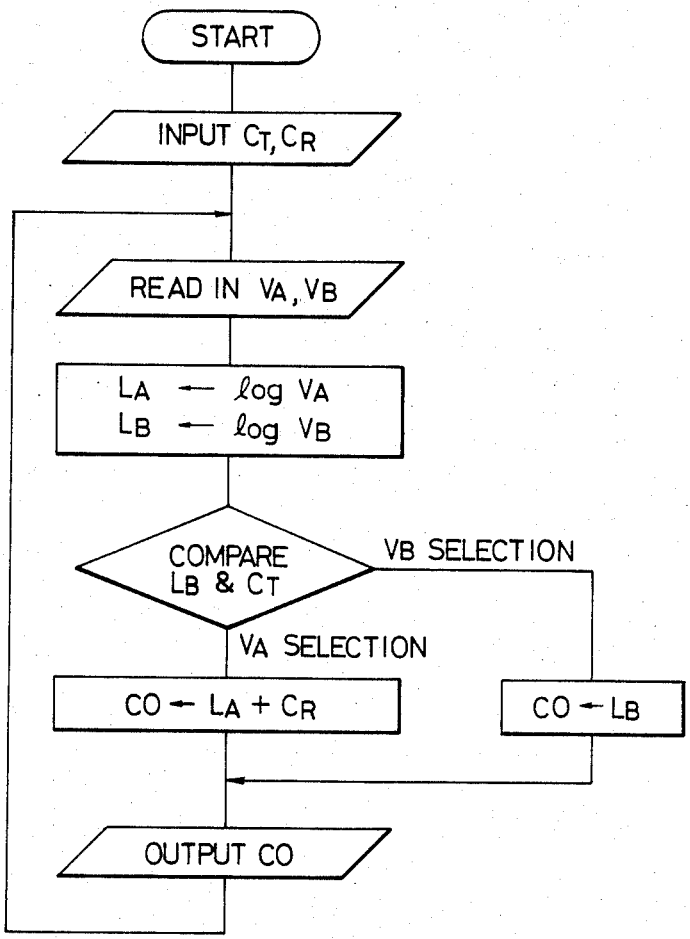
FIG. 13 is a flow chart of a program which may be utilized in the computer shown in FIG. 12.

10 by operating the digital computer in accordance with a program whose flow chart is shown in FIG. 13.

Though this invention was described with reference to various embodiments, this invention should not be limited to the embodiments, but can be modified in any extent without departing from the scope of this invention. For instance, the adder 25 or digital adder 32 in signal composing circuit 3 can be replaced by a multiplier or digital multiplier disposed before the logarithmic converters 22 and 23 or digital logarithmic converters 29 and 30.

As described hereinabove, in accordance with this invention, even though the variation in quantity of the ray bundle from each picture element, bearing the picture information, is extended over a wide dynamic range, all the picture information which the picture or image intrinsically carries can be read out.

What is claimed is:

1. An image reader comprising
at least two detection systems for scanning elements of a picture to be read and detecting light from each picture element where the detection systems differ from one another in detection sensitivity where the detection sensitivity of the first of said two detection systems extends from a minimum value to a maximum value and the sensitivity of the second of said two detection systems extends from a minimum value to a maximum value and where the maximum value of sensitivity of said first detection system is greater than the minimum value of sensitivity of said second detection system but less than the maximum value of sensitivity of said second detection system and where each of the said detecting systems develops an output signal, the amplitude of which corresponds to the quantity of light received from each of said elements of the picture and where said output signal amplitude corresponds to the sensitivity range for its associated detection system, and
a signal composing circuit responsive to the output signals from said detection systems and composing therefrom a time-serial signal, the amplitude variation of which is such that the amplitude can correspond to values extending from said minimum value of the first detection system sensitivity to the maximum value of the second detection system sensitivity whereby the sensitivity of the image reader is thus effectively expanded from the minimum value of the first detection system to the maximum value of the second detection system.

2. An image reader comprising
a high sensitive detection system for detecting a variation in a first light quantity to generate a first output,
a low sensitive detection system for detecting a variation in a second light quantity to generate a second output where said second light quantity is larger than said first light quantity, and
a signal composing circuit for receiving the outputs of said high and low sensitive detection systems,
each of said detection systems being so disposed as to detect simultaneously or substantially simultaneously a ray bundle from a picture element of a picture, and
the output of said signal composing circuit being (a) the output of said high sensitive detection system when the received light quantity is smaller than a threshold light quantity which can be detected with substantially the same degress of accuracy by both said detection systems or (b) the sum of (i) the output of said low sensitive detection system and (ii) the difference between the outputs of said detection systems at said threshold light quantity whereby a time-serial output of wide dynamic range is obtained.

* * * * *